(12) United States Patent
Yamasaki

(10) Patent No.: US 11,634,287 B2
(45) Date of Patent: Apr. 25, 2023

(54) DRIVE MECHANISM CAPABLE OF DEALING WITH GAS STERILIZATION

(71) Applicant: RORZE LIFESCIENCE INC., Tsukuba (JP)

(72) Inventor: Yukito Yamasaki, Tsukuba (JP)

(73) Assignee: RORZE LIFESCIENCE INC., Ibaraki (JP)

( * ) Notice: Subject to any disclaimer, the term of this patent is extended or adjusted under 35 U.S.C. 154(b) by 54 days.

(21) Appl. No.: 17/369,907

(22) Filed: Jul. 7, 2021

(65) Prior Publication Data

US 2022/0033201 A1 Feb. 3, 2022

Related U.S. Application Data

(63) Continuation of application No. PCT/JP2019/046623, filed on Nov. 28, 2019.

(30) Foreign Application Priority Data

Jan. 11, 2019 (JP) .............................. JP2019-003801

(51) Int. Cl.
*B65G 54/02* (2006.01)
*C12M 1/00* (2006.01)
*C12M 3/00* (2006.01)

(52) U.S. Cl.
CPC ............... *B65G 54/02* (2013.01); *C12M 1/00* (2013.01); *C12M 3/00* (2013.01)

(58) Field of Classification Search
CPC ............ B65G 54/02; C12M 1/00; C12M 3/00
(Continued)

(56) References Cited

U.S. PATENT DOCUMENTS 7,131,528 B1 * 11/2006 Rathgeber .......... B65G 21/2009
198/690.1
2011/0124093 A1 5/2011 Yamashita
(Continued)

FOREIGN PATENT DOCUMENTS

JP 9-322520 * 12/1997 .......... H02K 41/035
JP 2013128462 A 7/2013
(Continued)

OTHER PUBLICATIONS

International Search Report in PCT Application No. PCT/JP2019/046623, dated Feb. 18, 2020, 10pp.

*Primary Examiner* — James R Bidwell
(74) *Attorney, Agent, or Firm* — Hauptman Ham, LLP

(57) ABSTRACT

Provided is a drive mechanism capable of withstanding sterilization treatment using a sterilization gas such as hydrogen peroxide and capable of performing positioning operation with heightened accuracy. In a drive mechanism according to the invention, a movable block disposed in the internal space of a partition wall for blocking a sterilization gas is coupled to a movable platform disposed in the external space of the partition wall by means of a magnet coupling mechanism. Further, biasing magnet units are disposed on surfaces, of the movable block and the movable platform, on which no magnet coupling mechanism is disposed, such that the biasing magnet units serve as magnetic poles repelling each other. Repelling force generated by the biasing magnet units serves as biasing force that biases the movable platform toward the partition wall.

21 Claims, 14 Drawing Sheets

(58) Field of Classification Search
USPC .......................................................... 198/805
See application file for complete search history.

(56) References Cited

U.S. PATENT DOCUMENTS

| 2014/0054136 A1* | 2/2014 | Maeda ............. H01L 21/67709 |
| | | 198/750.1 |
| 2014/0117824 A1 | 5/2014 | Hayami |
| 2016/0228606 A1 | 8/2016 | Danti et al. |

FOREIGN PATENT DOCUMENTS

| JP | WO2012173074 A1 | | 2/2015 | |
| JP | 5903265 B2 | | 4/2016 | |
| JP | 2016533189 A | | 10/2016 | |
| JP | 2021016206 | * | 2/2021 | ............. H02J 50/05 |
| KR | 20110073968 | * | 6/2011 | ............. B65G 54/02 |
| WO | 2008/075616 | * | 6/2008 | ............. B65G 54/02 |
| WO | 2010001873 A1 | | 1/2010 | |
| WO | 2017126535 A1 | | 7/2017 | |

* cited by examiner

FIG. 7A
Mg1,3
| S | N |
|---|---|
| N | S |
| S | N |
Mg2,4
| S | N |
|---|---|
| N | S |
| S | N |
FIG. 7B
Mg1,3
| S | N | S |
|---|---|---|
| N | S | N |
| S | N | S |
Mg2,4
| N | S | N |
|---|---|---|
| S | N | S |
| N | S | N |
FIG. 7C
Mg1,3 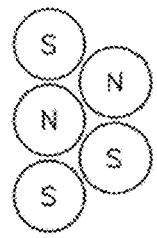
Mg2,4 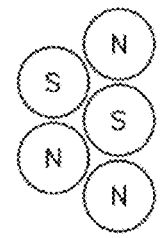

DRIVE MECHANISM CAPABLE OF DEALING WITH GAS STERILIZATION

RELATED APPLICATIONS

The present application is a continuation of International Application No. PCT/JP2019/046623, filed Nov. 28, 2019, which claims priority from Japanese Patent Application No. 2019-003801, filed Jan. 11, 2019 the disclosures of which applications are hereby incorporated by reference here in their entirety.

TECHNICAL FIELD

The present invention relates to a linear motion mechanism capable of operating with high accuracy and without failure even when exposed to a highly corrosive gas atmosphere such as hydrogen peroxide gas.

BACKGROUND ART

In the fields of drug discovery and regenerative medicine, an aseptic work apparatus such as a safety cabinet and an isolator is used for cell culture, various tests, and so on. As represented in the field of regenerative medicine, a series of work such as cell seeding, medium exchange, and observation requires high cleanliness without contamination. In addition, such a series of work is performed in a sterilized and clean environment in the aseptic work apparatus. The culture and testing are carried out with continuity for a long period of time. Indispensable in the process thereof is work such as sample condition grasping and medium exchange at a predetermined timing.

In addition, the cell seeding and medium exchange performed in the aseptic work apparatus of the related art have been manually performed by a worker. In recent years, however, a device for automating such work has been disposed in the aseptic work apparatus in the interest of work efficiency. Patent Document 1 discloses a dispensing device 50 disposed in the internal space of an isolator as illustrated in FIG. 1.

CITATION LIST

Patent Document

Patent Document 1: JP 5903265 B2

The dispensing device 50 disclosed in Patent Document 1 includes a slide device 64 that drives a syringe 61 to slide in the up-down direction and a rotating device 65 that rotates the syringe 61 in the X-axis and Y-axis directions. The drive device itself is reduced in size by each pivot shaft of the rotating device 65 being disposed so as to be orthogonal. Further, it is possible to improve the degree of freedom in terms of the positions of disposition of a placement platform 51 and a storage container A1 by reducing the size of the drive device, and thus the storage container A1 is disposed at a position where particles generated as a result of drive device operation are not mixed. As a result, it has become possible to prevent particle contamination attributable to drive device operation to culture object and solution.

SUMMARY OF THE INVENTION

Problem to be Solved by the Invention

By the way, in recent years, treatment has been performed by a gas sterilization method for performing decontamination by filling the work space of the aseptic work apparatus with an oxidizing gas. Hydrogen peroxide gas sterilization, in particular, has been widely implemented as the sterilization time is relatively short and the sterilization is safe because oxygen-hydrogen decomposition follows the sterilization. In the aseptic work apparatus, the sterilization in the case of handling different types of cells is performed after each work so that various germs and contaminants that have intruded from the external environment are removed and cross-contamination is prevented. However, hydrogen peroxide has a strong corrosive action, and thus the sterilization treatment object is limited to a material resistant to corrosion. In the dispensing device 50 of Patent Document 1, the drive mechanism driving the syringe 61 and the storage container A1 is installed in an exposed state. In the case of sterilization by means of a sterilization gas such as hydrogen peroxide gas, a sterilization gas component adheres to the exposed mechanism part and corrodes, and then it is impossible to continue with the work.

The invention has been made in view of the above problems, and an object of the invention is to provide a drive mechanism capable of withstanding sterilization treatment using a sterilization gas such as hydrogen peroxide and capable of performing positioning operation with heightened accuracy.

Means for Solving Problem

In order to achieve the above object, the drive mechanism of the invention includes a movable block, a drive unit moving the movable block, a guide mechanism guiding the movable block in a predetermined direction, a partition wall isolating the movable block, the drive unit, and the guide mechanism from an external environment, a movable platform provided outside the partition wall and at a position facing the movable block via the partition wall so as to cover at least a part of the partition wall and be movable along the partition wall, a first magnet coupling mechanism including magnets attracting each other on surfaces (first surfaces) mutually facing the movable block and the movable platform via the partition wall, and a second magnet coupling mechanism including magnets attracting each other and provided on surfaces (second surfaces) of the movable block and the movable platform orthogonal to the first surfaces and facing each other via the partition wall, in which the movable platform moves on a trajectory guided by the partition wall by following the movement of the movable block.

The drive mechanism may be configured to include a rolling body rollably attached to the surface of the movable platform facing the partition wall. In addition, the drive mechanism is capable of including biasing magnet units provided with magnetic poles repelling each other in a direction of reinforcement of attractive force of the first and/or second magnet coupling mechanism on surfaces (third surfaces) of the movable block and the movable platform different from the first and second surfaces as surfaces of the movable block and the movable platform facing each other via the partition wall. As a result, the movable platform is capable of more accurately moving on the trajectory guided by the partition wall.

In addition, the magnets constituting the first magnet coupling mechanism and the second magnet coupling mechanism are permanent magnets. Further, the magnets constituting the first magnet coupling mechanism and the second magnet coupling mechanism may include an electromagnet.

In addition, the surfaces of the movable block and the movable platform where the biasing magnet units are disposed may be disposed so as to be inclined at a predetermined angle with respect to the surfaces where the second magnet coupling mechanism is disposed. With the above configuration, the biasing force generated by the biasing magnet units is capable of acting on both the first magnet coupling mechanism and the second magnet coupling mechanism, and thus the movable platform is capable of more accurately moving on the trajectory guided by the partition wall.

In addition, the drive mechanism of the invention can be used at a moving part of a distribution device, a medium exchange device, or a cultured cell handling device and has corrosion resistance, and thus the device can be operated with stability and without corrosion even if the entire device is sterilized with an oxidizing gas.

Effect of the Invention

According to the configuration of the invention, the sealability of a movable part is enhanced, and thus gas sterilization by means of an oxidizing gas can be used. Accordingly, the effect of preventing contamination attributable to various germs and the like is high and a stable device operation for a long period of time can be achieved. In addition, the movable platform can be accurately positioned, and thus an accurate forward-backward operation, which is impossible with the device of the related art, can be performed with stability for a long period of time.

BRIEF DESCRIPTION OF DRAWINGS

FIGS. 7A to 7C are schematic diagrams illustrating the disposition of each magnet in the magnet unit included in the drive mechanism of the invention;

MODE(S) FOR CARRYING OUT THE INVENTION

Figure 1:
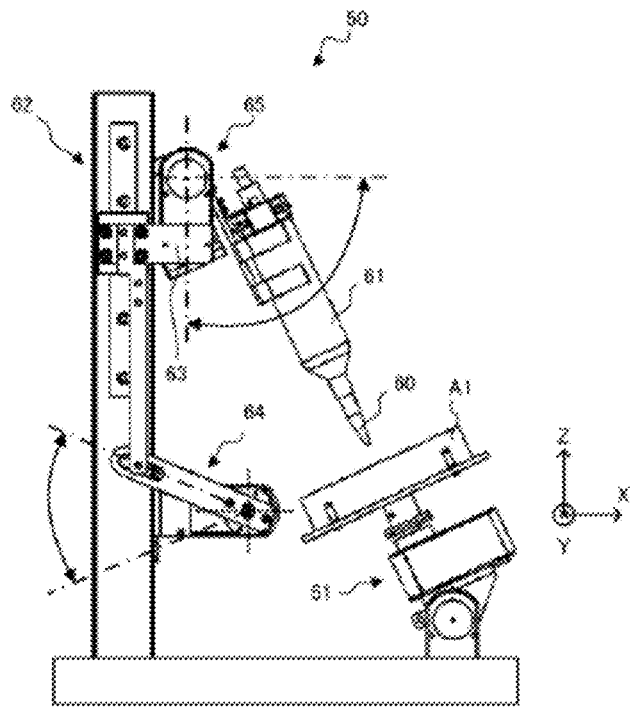
FIG. 1 is a diagram illustrating a dispensing device as an example including a drive mechanism of the related art.
Figure 2:
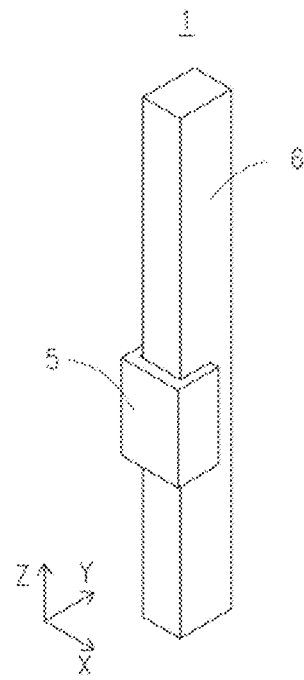
FIG. 2 is a perspective view illustrating a drive mechanism according to an embodiment of the invention.
Figure 3:
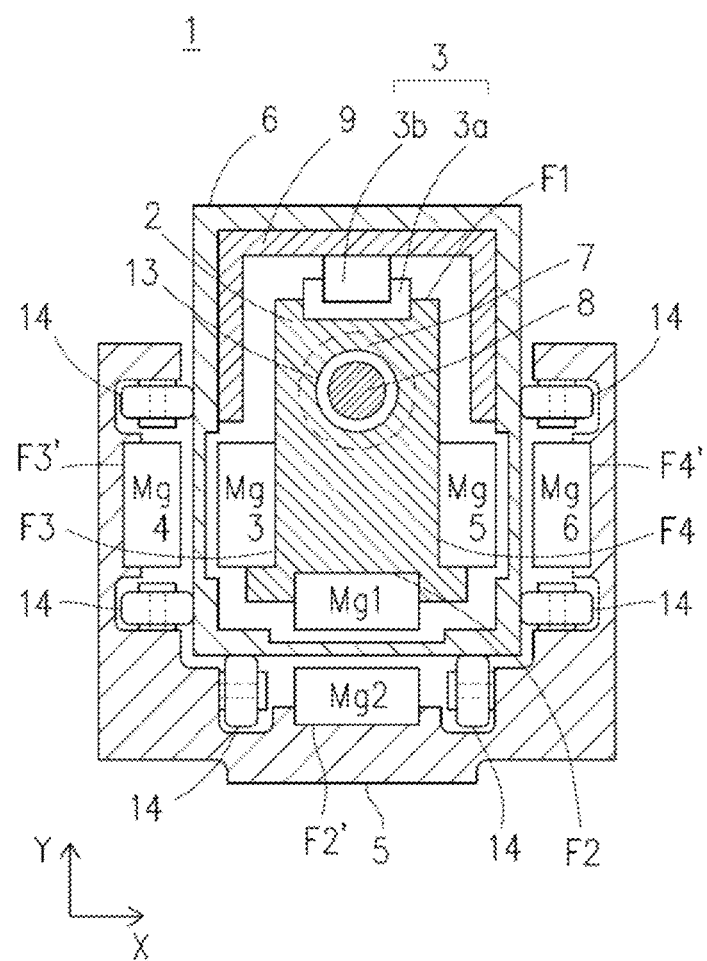
FIG. 3 is a sectional view of the drive mechanism according to an embodiment of the invention in the XY plane.
Figure 4:
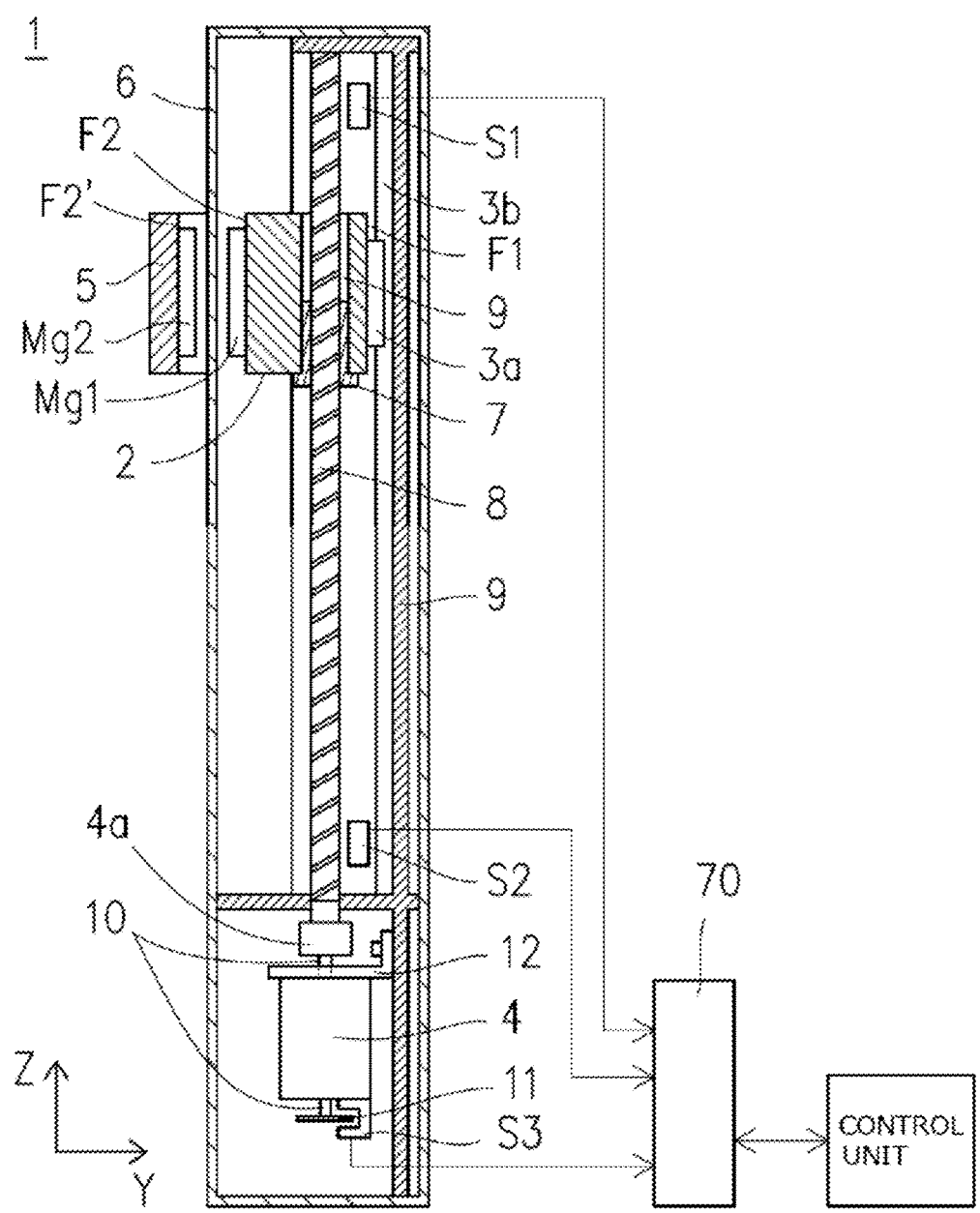
FIG. 4 is a sectional view of the drive mechanism according to an embodiment of the invention in the YZ plane.

Details of the invention will be described in detail below with reference to the drawings. FIG. 2 is a perspective view illustrating a drive mechanism 1 according to an embodiment of the invention, FIG. 3 is a diagram illustrating a cross section of the movable platform 5 part of the drive mechanism 1 in the XY plane, and FIG. 4 is a diagram illustrating a middle longitudinal section of the drive mechanism 1 in the YZ plane. The drive mechanism 1 of the invention includes a movable block 2 that moves by an internal screw shaft 8 rotating, a guide mechanism 3 that guides the movable block 2 in a predetermined direction, a drive source 4 that moves the movable block 2 by rotationally driving the screw shaft 8, and the movable platform 5 that moves together with the movable block 2. In addition, the movable block 2, the guide mechanism 3, and the drive source 4 are disposed in a space isolated from the external environment (external environment in a device such as a distribution device: hereinafter, referred to as "work space": corresponding to a work space 36 to be described later) by a partition wall 6 and the movable platform 5 is disposed outside the partition wall 6 (in the work space).

In addition, the movable block 2 and the movable platform 5 include a first drive magnet unit Mg1 and a first driven magnet unit Mg2 and a second drive magnet unit Mg3 and a second driven magnet unit Mg4 disposed so as to be attracted to each other by magnetic force via the partition wall 6. The movable platform 5 follows the movement of the movable block 2 and moves along the partition wall 6 as a result of the magnet coupling attributable to the attractive force of the magnet units Mg1 to Mg4.

Further, a first biasing magnet unit Mg5 and a second biasing magnet unit Mg6, which are disposed so as to repel each other by mutual magnetic force, are provided on the surfaces of the movable block 2 and the movable platform 5 on the side opposite to the surfaces where the second drive magnet unit Mg3 and the second driven magnet unit Mg4 are disposed (right side in FIG. 3). The repelling force generated by the biasing magnet units Mg5 and Mg6 disposed so as to repel each other serves as biasing force providing biasing and reinforcement in the same direction as the attractive force attributable to the magnet coupling between the movable block 2 and the movable platform 5, and thus the distance of the movable platform 5 to the partition wall 6 can be kept constant.

The guide mechanism 3 included in the drive mechanism 1 of the present embodiment includes a guide rail 3b that guides a mover 3a fixed to the movable block 2 in a predetermined direction, the screw shaft 8 that is disposed so as to be parallel to the guide rail 3b and screwed into a ball nut 7 fixed to the movable block 2, and a motor 4 that is a drive source coupled to the screw shaft 8 and rotationally driving the screw shaft 8. The guide rail 3b is fixed to one surface of the internal space of a casing 9, which is the base of the drive mechanism 1, and the screw shaft 8 is rotatably fixed to the casing 9. In addition, the casing 9 provided with the guide mechanism 3 of the present embodiment has a vertically long substantially rectangular parallelepiped shape and the motor 4 is fixed to one end portion of the casing 9 via a bracket 12. In the motor 4 included in the guide mechanism 3 of the present embodiment, a rotating shaft 10 is concentrically coupled to the screw shaft 8 via a coupling 4a. By the rotating shaft 10 of the motor 4 performing rotational operation, the screw shaft 8 also performs rotational operation.

Position detection sensors S1 and S2, which detect the position of the movable block 2, are provided on the longitudinal wall surface of the casing 9. In addition, an optical rotation detection sensor S3 detecting the rotation angle of the rotating shaft 10 of the motor 4 is provided in the vicinity of the motor 4 and a sensor dog 11 fixed to the rotating shaft 10 detects the rotational position of the rotating shaft 10 by blocking the optical axis of the rotation detection sensor S3. These sensors S1, S2, and S3 are connected to a control unit 70 that controls the rotation of the motor 4. It should be noted that the motor 4 included in the drive mechanism 1 of the present embodiment is a stepping motor with which the rotation angle of the rotating shaft 10 is controlled with ease and the rotation of the rotating shaft 10 is controlled by a control signal from the control unit 70. In addition, although a transmitted light-type sensor, a reflected light-type sensor, a magnetic sensor, and so on can be applied as the position detection sensors S1 and S2 detecting the movable block 2, a sensor using another detection method may be used instead.

In the embodiment exemplified in FIGS. 1 to 6, the movable block 2 included in the drive mechanism 1 has a substantially rectangular parallelepiped shape and the mover 3a of the guide rail 3b is fixed to a surface F1 facing the guide rail 3b. In addition, a hole 13 penetrated by the screw shaft 8 is formed in the movable block 2 and the ball nut 7 screwed with the screw shaft 8 is fixed to the movable block 2 in a state of being inserted in the hole 13. With this configuration, the movable block 2 is capable of moving in the plane guided by the guide rail 3b in conjunction with the rotation of the screw shaft 8.

In addition, the first drive magnet unit Mg1 is fixed to a surface F2 (front surface) on the side opposite to the surface F1 where the mover 3a of the movable block 2 is fixed. Further, the first driven magnet unit Mg2 is fixed, so as to be parallel to the first drive magnet unit Mg1, to a surface F2' of the movable platform 5 facing the front surface F2 of the movable block 2. The first drive magnet unit Mg1 and the first driven magnet unit Mg2 constitute a first magnet coupling mechanism using attractive force generated by different magnetic poles facing each other.

In addition, the second drive magnet unit Mg3 is fixed to a left side surface (first side surface) F3 formed substantially at right angles to the front surface F2 of the movable block 2. Further, the second driven magnet unit Mg4 is fixed, so as to be parallel to the second drive magnet unit Mg3, to a left side surface (first side surface) F3' of the movable platform 5 facing the first side surface F3 of the movable block 2 via the partition wall 6. The second drive magnet unit Mg3 and the second driven magnet unit Mg4 constitute a second magnet coupling mechanism using attractive force generated by different magnetic poles facing each other.

Further, the first biasing magnet unit Mg5 is disposed on a right side surface (second side surface) F4 formed on the side opposite to the first side surface F3 of the movable block 2. In addition, the second biasing magnet unit Mg6 is fixed, so as to be parallel to the first biasing magnet unit Mg5, to a right side surface (second side surface) F4' of the movable platform 5 facing the second side surface F4 of the movable block 2 via the partition wall 2. In the first biasing magnet unit Mg5 and the second biasing magnet unit Mg6, magnetic fields repelling each other are formed by the same magnetic poles facing each other. The second side surface F4' of the movable platform 5 is biased away from the second side surface F4 of the movable block 2 such that the repelling force generated by the first biasing magnet unit Mg5 and the second biasing magnet unit Mg6 reinforces the attractive force of the second magnet coupling (attractive force acting so as to bring the movable platform 5 into close contact with the partition wall 6 side close to the first side surface F3 of the movable block 2). The first biasing magnet unit Mg5 and the second biasing magnet unit Mg6 can be selectively added in a case where it is desirable to reinforce the attractive force of the first and/or second magnet coupling mechanism.

The partition wall 6 included in the drive mechanism 1 of the present embodiment is a box-shaped member airtightly isolating the movable block 2, the guide mechanism 3, and the motor 4 from the work space and is fixed to the casing 9. The inside of the space defined by the partition wall 6 is maintained in a general air atmosphere. Even if the work space is filled with an oxidizing gas atmosphere such as hydrogen peroxide gas, the guide mechanism 3 disposed in the internal space of the partition wall 6 is capable of operating normally without being affected by the corrosive action attributable to the oxidizing gas atmosphere.

The movable platform 5 included in the drive mechanism 1 exemplified in the present embodiment is a member having a substantially U-shaped section and is disposed so as to cover the partition wall 6 in the external environment outside the space defined by the partition wall 6. In addition, a plurality of rolling bodies 14 are attached to each of the front surface F2', the first side surface F3', and the second side surface F4', which are the surfaces of the movable platform 5 of the present embodiment that face the partition wall 6. The rolling body 14 of the present embodiment is a member that supports the movable platform 5 against the magnetic attractive force generated by the magnet units Mg1 to Mg4 and keeps the distance between the partition wall 6 and the movable platform 5 constant. Further, the rolling body 14 of the present embodiment is a member that reduces the sliding resistance of the movable platform 5 sliding and moving on the partition wall 6. By the rolling body 14 being provided on the surface facing the partition wall 6, the movable platform 5 is capable of following the movement of the movable block 2 and moving on the partition wall 6 without the main body of the movable platform 5 coming into contact with the partition wall 6.

Figure 5:
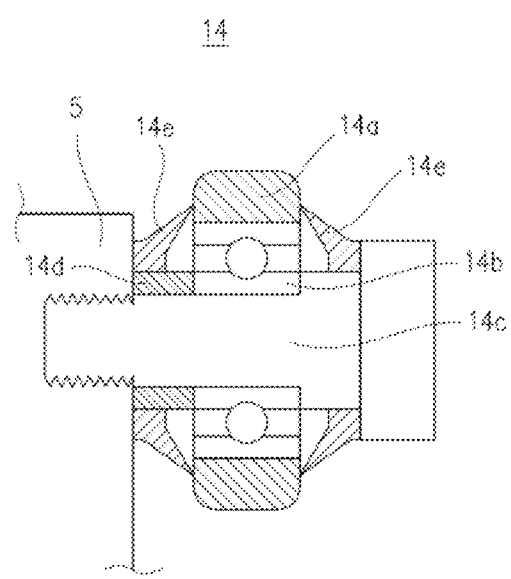
FIG. 5 is a sectional view illustrating a rolling body included in the drive mechanism of the invention.

FIG. 5 is a sectional view exemplifying the rolling body 14 included in the drive mechanism 1 of the present embodiment. The rolling body 14 of the present embodiment includes an annular wheel member 14a formed of a resin material, a bearing 14b inserted into the wheel member 14a, a stainless steel shaft 14c inserted into the inner ring of the bearing 14b, a collar 14d disposed between the inner ring of the bearing 14b and the movable platform 5, and a seal packing 14e substantially having a funnel shape. The seal packing 14e is disposed on both side surfaces of the wheel member 14a. Further, the peripheral edge of the lip part at the tip of the seal packing 14e is in airtight contact with the wheel member 14a. As a result, the space where the bearing 14b is disposed is isolated from the work space by the wheel member 14a and the seal packing 14e and oxidizing gas particles are prevented from coming into contact with the bearing 14b.

It should be noted that the annular wheel member 14a is desirably formed of an engineering plastic material having high wear resistance and chemical resistance, examples of which include polyetheretherketone (PEEK), polyphenylene sulfide (PPS), and Vespel (registered trademark). In addition, the seal packing 14e is desirably formed of a flexible material having excellent heat resistance and chemical resistance, examples of which include fluororubber, acrylic rubber, hydrogenated nitrile rubber, silicone resin, vinyl acetate ethylene resin, and ethylene propylene rubber.

Figure 6A:
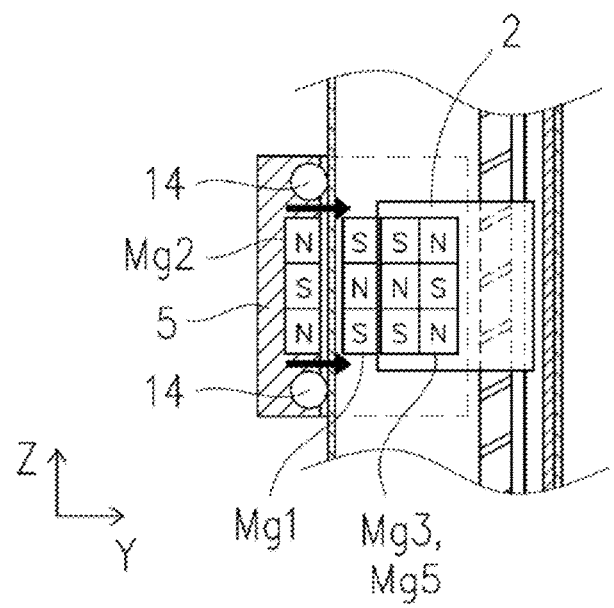
FIGS. 6A and B are schematic sectional views illustrating the disposition of a magnet unit included in the drive mechanism of the invention.
Figure 6B:
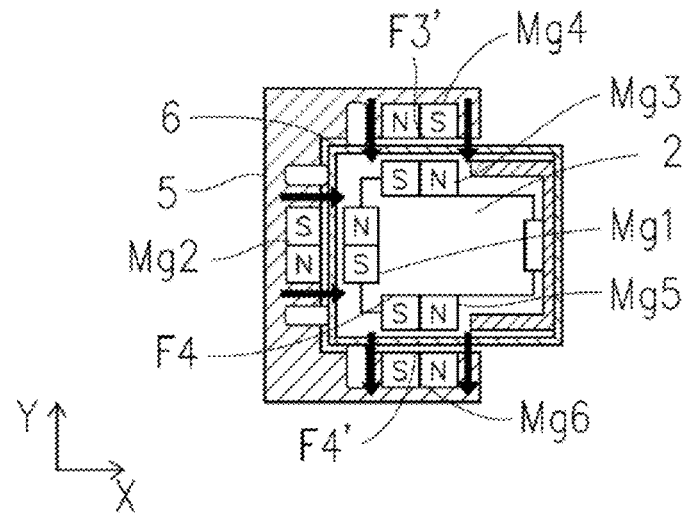

Next, the magnet units Mg1 to Mg4 of the present embodiment will be described. FIGS. 6A and 6B are schematic sectional views illustrating the disposition of the permanent magnets of the magnet units Mg1 to Mg4 included in the drive mechanism 1 of the present embodiment. FIG. 6A is a vertical partial sectional view illustrating the polar disposition of the permanent magnets of the movable block 2 and the movable platform 5 of the drive mechanism 1, and FIG. 6B is a cross-sectional view. The magnet units Mg1 to Mg4 of the present embodiment are disposed in a grid pattern such that the rectangular permanent magnets have different polarities next to each other. In addition, the magnet units Mg1 to Mg4 disposed so as to face each other are configured such that magnetic poles on which attractive force acts are disposed with respect to the magnetic poles of the facing magnets. With this configuration, the movable platform 5 is biased in the direction indicated by the arrow in the drawing by the attractive force between the magnets with different magnetic poles disposed so as to face each other and the positions of the movable block 2 and the movable platform 5 can be effectively maintained at predetermined positions. In addition, even in a case where the positional relationship between the drive magnet units Mg1 and Mg3 and the driven magnet units Mg2 and Mg4 is likely to deviate by some load being applied to the movable platform 5, the magnets of the same pole disposed next to each other repel each other, and thus each magnet functions to return the position of the movable platform 5 to a predetermined position.

FIGS. 7A to 7C are diagrams exemplifying the polarities at a time when each of the disposition of the drive magnet units Mg1 and Mg3 and the disposition of the driven magnet units Mg2 and Mg4 is viewed from the partition wall 6 side. The shape and disposition of the magnets used in the magnet units Mg1 to Mg4 are not limited to the embodiment in which the permanent magnets are disposed in two rows as illustrated in FIG. 7A. For example, the permanent magnets can also be disposed in three rows as illustrated in FIG. 7B or magnets having a circular sectional shape can also be disposed in a houndstooth pattern as illustrated in FIG. 7C. In addition, it is sufficiently possible that the sectional shape of the magnet is a non-rectangular and non-circular shape. Further, a yoke that increases the attractive force may be attached to each magnet. It should be noted that a magnet with strong magnetic force, such as a neodymium magnet and a samarium cobalt magnet, is desirably used as the magnets used in the magnet units Mg1 to Mg4. In addition, the magnet such as the neodymium magnet and the samarium cobalt magnet is easy to corrode, and thus it is desirable that the surface of the magnet is treated with, for example, nickel resistant to a highly corrosive gas such as hydrogen peroxide gas or coated with a resistant material such as silicone.

Next, the first biasing magnet unit Mg5 and the second biasing magnet unit Mg6 of the present embodiment will be described. The biasing magnet units Mg5 and Mg6 of the present embodiment are disposed in a grid pattern such that the rectangular magnets have different polarities next to each other. In addition, the biasing magnet units Mg5 and Mg6 disposed so as to face each other are configured such that magnetic poles on which repelling force acts are disposed with respect to the magnetic poles of the facing magnets. See FIG. 6B. It should be noted that the shape and disposition of the magnets used in the biasing magnet units Mg5 and Mg6 are not limited to the above embodiment. For example, it is sufficiently possible that magnets having a circular sectional shape are disposed in a houndstooth pattern as described above and it is also sufficiently possible that the sectional shape of the magnet is a non-rectangular and non-circular shape. In addition, a yoke that increases the repelling force may be attached to each magnet. In addition, it is desirable to use a permanent magnet with strong magnetic force, such as a neodymium magnet and a samarium cobalt magnet, as the magnets used in the biasing magnet units Mg5 and Mg6. In addition, it is desirable that the surface of the magnet is treated with, for example, nickel resistant to a highly corrosive gas such as hydrogen peroxide gas or coated with a resistant material such as silicone.

By the way, the movable block 2 is configured to move in the plane guided by the guide mechanism 3 and no misalignment occurs in a direction orthogonal to the traveling direction. However, no mechanism guides the movable platform 5, the movable platform 5 is pressed against the partition wall 6 simply by the magnetic attractive force generated by the magnet units Mg1 to Mg4, and thus misalignment in a direction orthogonal to the traveling direction is likely to occur as the movable platform 5 moves. In this regard, the drive mechanism 1 of the present embodiment is configured to bias the repelling force generated by the first biasing magnet unit Mg5 and the second biasing magnet unit Mg6 in the direction of pressing the movable platform 5 against the partition wall 6. The direction of the biasing force that presses the movable platform 5 against the partition wall 6 is configured to be the same as the direction of the attractive force that attracts the movable platform 5 to the partition wall 6 by the magnet unit Mg3 and the magnet unit Mg4. As a result, the movable platform 5 is biased in the direction in which the surface F3' is pressed toward the partition wall 6 in addition to the magnetic attractive force of the magnet coupling mechanism of the magnet unit Mg3 and the magnet unit Mg4, and thus the movable platform 5 is capable of accurately moving on the trajectory guided by the partition wall 6.

The partition wall 6 of the present embodiment has a function of accurately guiding the direction of movement of the movable platform 5 in addition to a function of storing the guide mechanism 3, the drive source 4, and the movable block 2 having low resistance to a sterilization gas and isolating the guide mechanism 3, the drive source 4, and the movable block 2 from the work space filled with a sterilization gas during sterilization treatment. Further, the partition wall 6 of the present embodiment has a function of supporting the movable platform 5 against the repelling force generated by the magnet units Mg5 and Mg6 in addition to a function of supporting the movable platform 5 against the attractive force generated by the magnet units Mg1, Mg2, Mg3, and Mg4. In this regard, it is desirable to use a sturdy member for the partition wall 6 in order to counter such attractive force and repelling force. It should be noted that the partition wall 6 of the present embodiment is formed of stainless steel, which is highly resistant to corrosion and relatively tough. In addition, a large load is applied to the part where the rolling body 14 included in the movable platform 5 abuts, and thus the thickness of the member of the partition wall 6 may be increased along the trajectory through which the rolling body 14 passes for the structure to withstand the load. Further, a tough member may be disposed along the trajectory through which the rolling body 14 passes and members having high magnetic force transmission may be disposed along the trajectories through which the magnet units Mg1 to Mg6 pass with the respective members airtightly interconnected.

Figure 8:
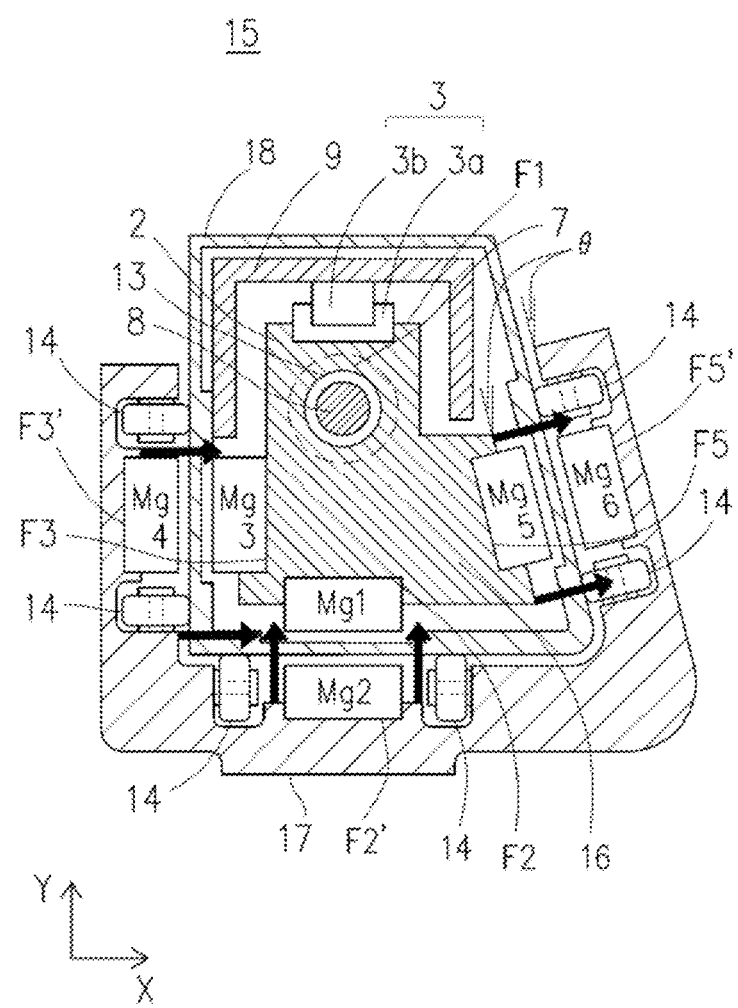
FIG. 8 is a diagram illustrating another embodiment of the drive mechanism of the invention.

Next, a drive mechanism 15 according to a second embodiment of the invention will be described. FIG. 8 is a diagram illustrating a section of the drive mechanism 15 of the present embodiment in the XY plane. It should be noted that common reference numbers are assigned to configurations identical to those of the drive mechanism 1 of the first embodiment. A movable block 16 included in the drive mechanism 15 of the present embodiment has the front surface F2 parallel to the X axis as in the case of the movable block 2 of the first embodiment and the first side surface F3 parallel to the Y-axis direction and perpendicular to the front surface F2. In addition, a movable platform 17 included in the drive mechanism 15 of the present embodiment has the front surface F2' parallel to the X axis as in the case of the movable platform 5 of the first embodiment and the first side surface F3' parallel to the Y-axis direction and perpendicular to the front surface F2'. In addition, as in the case of the first embodiment, the magnet units Mg1, Mg2, Mg3, and Mg4 are fixed to the front surfaces F2 and F2' and the first side surfaces F3 and F3' of the movable block 16 and the movable platform 17 and the first drive magnet unit Mg1 and the first driven magnet unit Mg2 are coupled to each other and the second drive magnet unit Mg3 and the second driven magnet unit Mg4 are coupled to each other by magnet coupling using magnetic poles having different polarities. Further, a partition wall 18 having wall surfaces respectively parallel to the front surfaces F2 and F2' and the first side surfaces F3 and F3' is disposed in the space between the first drive magnet unit Mg1 and the first driven magnet unit Mg2 and the space between the second drive magnet unit Mg3 and the second driven magnet unit Mg4. As in the case of the drive mechanism 1 of the first embodiment, the partition wall 18 stores the movable block 16, the guide mechanism 3, the ball screw mechanism 8, the drive source 4, and so on in the internal space airtightly isolated from the work space.

A second side surface F5, which is formed on the movable block 16 of the present embodiment, is formed so as to be tilted by θ degrees as compared with the movable block 2 of the first embodiment parallel to the Y-axis direction when viewed from above. In addition, a second side surface F5', which is formed on the movable platform 17 of the present embodiment, is formed so as to be tilted by θ degrees as compared with the movable platform 5 of the first embodiment parallel to the Y-axis direction when viewed from above. Correspondingly, the surface of the partition wall 18 of the present embodiment that is disposed between the movable block 16 and the movable platform 17 is also formed so as to be tilted by θ degrees as compared with the partition wall 6 of the first embodiment.

The first biasing magnet unit Mg5 is fixed to the second side surface F5 formed on the movable block 16 of the present embodiment. The second biasing magnet unit Mg6 is fixedly disposed, so as to face the first biasing magnet unit Mg5, on the second side surface F5' of the movable platform 17 facing the movable block 16. In a state of being tilted by θ degrees with respect to the Y-axis direction when viewed from above, the first biasing magnet unit Mg5 and the second biasing magnet unit Mg6 are fixed to the second side surfaces F5 and F5', respectively.

With the above configuration, the direction in which the biasing force generated by the first biasing magnet unit Mg5 and the second biasing unit Mg6 repelling each other acts is not parallel to the X-axis and Y-axis directions. In other words, the biasing force generated by the first biasing magnet unit Mg5 and the second biasing unit Mg6 has both a component by which the movable platform 17 is biased in the X-axis direction and a component by which the movable platform 17 is biased in the Y-axis direction, and thus the movable platform 17 is pressed in the Y-axis direction as well as the X-axis direction. As a result, the movable platform 17 is capable of moving, without misalignment, on the trajectory in the plane defined by the partition wall 18.

Figure 9A:
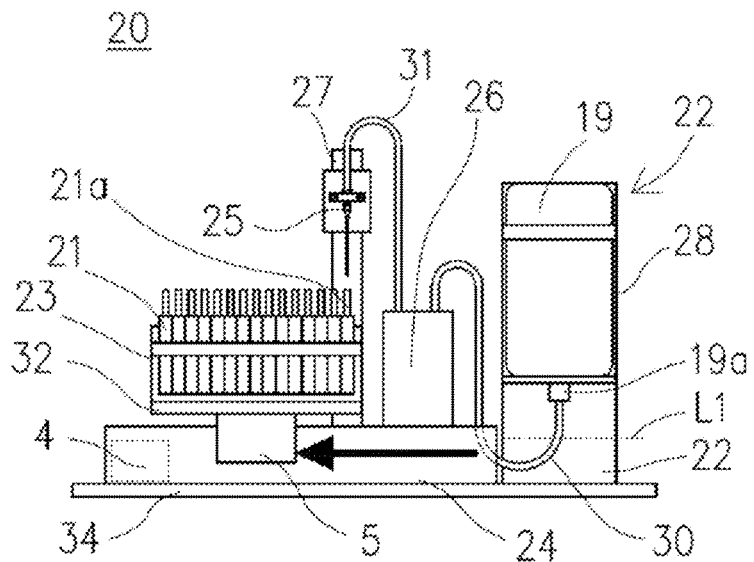
FIGS. 9A and 9B are front views illustrating a distribution device according to an embodiment of the invention.
Figure 9B:
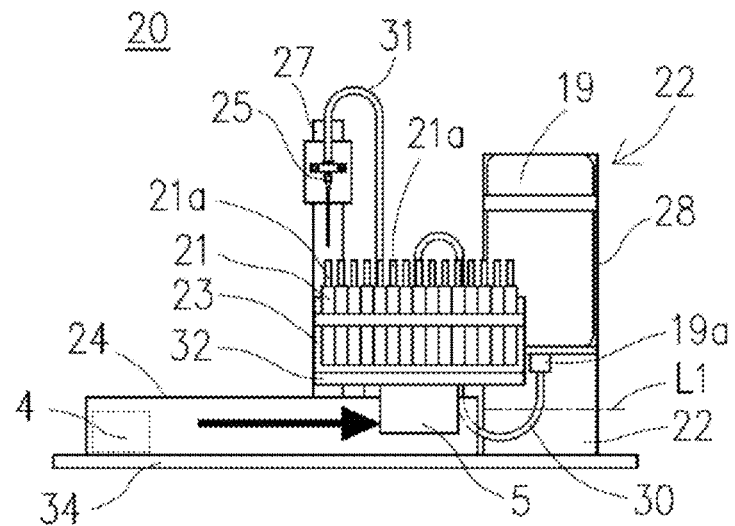
Figure 10A:
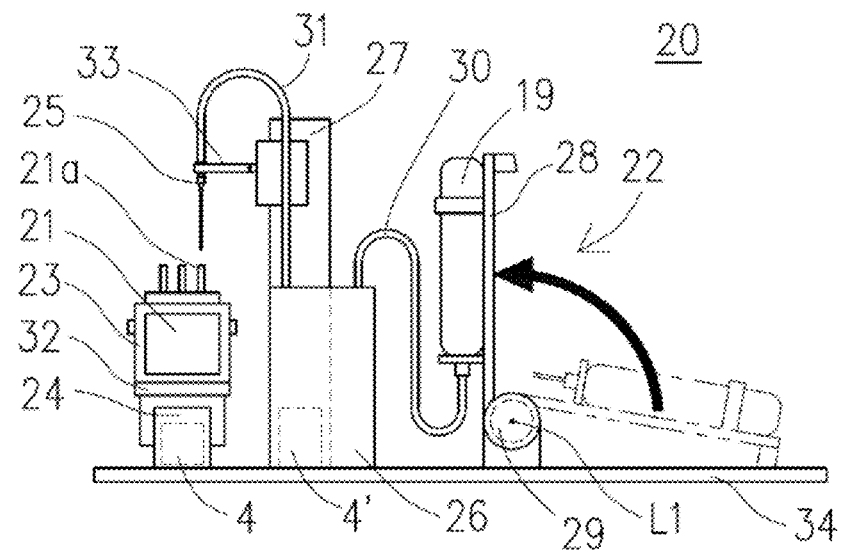
FIGS. 10A and 10B are side views illustrating the distribution device according to an embodiment of the invention.
Figure 10B:
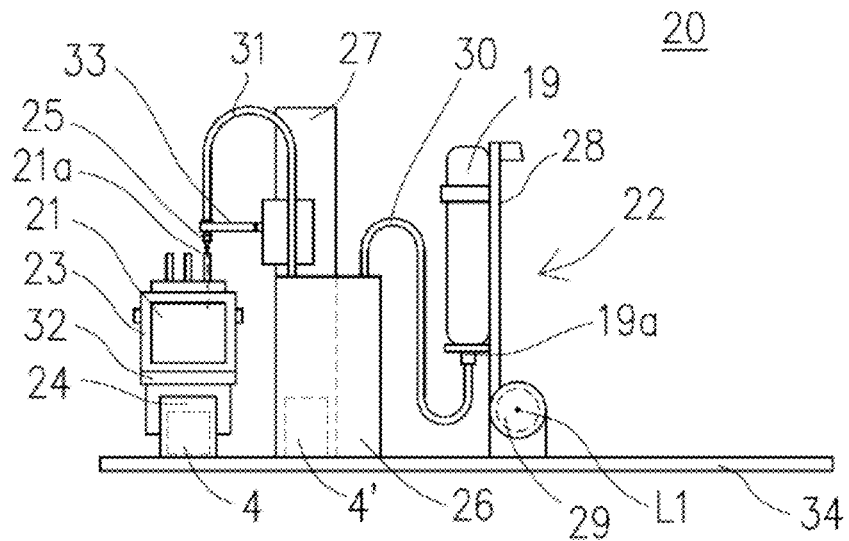

Next, a distribution device 20, which is an embodiment using the drive mechanism 1 of the invention, will be described. FIGS. 9A and 9B are front views illustrating the distribution device 20 of the present embodiment, and FIGS. 10A and 10B are side views thereof. The distribution device 20 of the present embodiment is a device for automatically distributing the medium (culture solution) with which a large-capacity container 19 is filled to a plurality of subdivision containers 21. The distribution device 20 of the present embodiment includes a container holding unit 22 that holds the large-capacity container 19 in an inverted state with a discharge port 19a facing downward, a container rack 23 that accommodates the plurality of subdivision containers 21, a rack moving unit 24 that moves the container rack 23 in the horizontal direction, a pump unit 26 that suctions the medium (culture solution) with which the container 19 is filled and discharges the medium (culture solution) from a nozzle 25, and a nozzle lifting-lowering unit 27 that moves the nozzle 25 up and down in the vertical direction.

The container holding unit 22 of the present embodiment includes a tray portion 28 that holds the large-capacity container 19 and a drive source 29 that rotates the tray portion 28 with a horizontally extending rotation axis L1 as the center of rotation. When the large-capacity container 19 is fixed to the tray portion 28, the tray portion 28 is laid down, the container 19 is fixed to the tray portion 28, a suction tube 30 is connected to the discharge port 19a of the container 19, and then the tray portion 28 is caused to stand upright by the drive source 29 being rotated. Subsequently, the container 19 is maintained in the inverted state with the discharge port 19a facing downward.

A pump (not illustrated) is included in the pump unit 26. The pump suctions the medium (culture solution) with which the container 19 is filled via the suction tube 30 and discharges the medium (culture solution) from the nozzle 25 via a discharge tube 31. It should be noted that the pump (not illustrated) is a known pump and it is preferable to use a pump such as a peristaltic pump and a piezoelectric pump relatively easy to decontaminate and unlikely to contaminate a sample.

The drive mechanism 1 of the invention is used in the rack moving unit 24 and the nozzle lifting-lowering unit 27 of the distribution device 20. The rack moving unit 24 is disposed in a state where the drive mechanism 1 of the invention is laid down in the horizontal direction such that the front surface of the movable platform 5 faces upward. A rack placement platform 32 is fixed to the upper surface of the movable platform 5, and the container rack 23 is detachably attached at a predetermined position of the rack placement platform 32. In the container rack 23, the plurality of subdivision containers 21 are disposed side by side in the left-right direction in the drawing with injection ports 21a facing upward. The container rack 23 is fixed at a predetermined position on the rack placement platform 32. It should be noted that the subdivision container 21 is provided with three cylindrical ports, the two ports other than the injection port 21a are used for, for example, taking out the medium injected in the subdivision container 21, and the two ports are airtightly closed when the medium is injected from the injection port 21a. FIG. 9A is a diagram illustrating where the injection port 21a of the subdivision container 21 disposed at the right end of the container rack 23 in the drawing is positioned directly below the nozzle 25, and FIG. 9B is a diagram illustrating where the injection port 21a of the subdivision container 21 disposed at the left end of the container rack 23 is positioned directly below the nozzle 25. The rack moving unit 24 has a stroke that is sufficient to move all the subdivision containers 21 accommodated in the container rack 23 to directly below the nozzle 25 by moving the movable platform 5 in the horizontal direction. The position information of the motor 4 for moving each of the subdivision containers 21 to directly below the nozzle 25 is taught in advance by a worker, and the position information is stored in the control unit 70.

The nozzle lifting-lowering unit 27, which moves the nozzle 25 up and down in the vertical direction, includes the drive mechanism 1 of the invention in a vertically erected state. A nozzle bracket 33 fixing the nozzle 25 is fixed to the movable platform 5. The nozzle lifting-lowering unit 27 is disposed at a position where the nozzle 25 can be inserted through the injection port 21a of the subdivision container 21 accommodated in the container rack 23 when the nozzle 25 is lowered. In addition, the drive mechanism 1 provided in the nozzle lifting-lowering unit 27 has a stroke at which the tip of the nozzle 25 is capable of reaching the vicinity of the middle portion of the subdivision container 21 when the nozzle 25 is lowered and moving up to a position where the upper end portion of the subdivision container 21 and the tip portion of the nozzle 25 do not interfere with each other. The tip of the discharge tube 31 is connected to the base end portion of the nozzle 25, and the medium (culture solution) supplied from the pump unit 26 is supplied to the nozzle 25 and injected into the subdivision container 21. The position information of a motor 4' for moving the nozzle 25 to the ascending and descending positions is taught in advance by a worker, and the position information is stored in the control unit 70.

The operation of the motor 4 of the rack moving unit 24, the motor 4' of the nozzle lifting-lowering unit 27, the drive source 29 of the container holding unit 22, and the pump of the pump unit 26 is controlled by a distribution device control unit (not illustrated). The distribution device control unit includes at least a known computer, a storage unit that stores an operation program and various pre-taught data, and a communication unit that communicates with a higher-side host computer. The distribution device control unit operates each drive mechanism by receiving an input signal from each sensor and transmitting an operation command to the control unit included in each unit in accordance with the pre-stored operation program. With the above configuration, the distribution device 20 of the present embodiment is capable of sequentially and automatically distributing the medium (culture solution) with which the large-capacity container 19 is filled to the plurality of subdivision containers 21 stored in the container rack 23. The control unit 70 of the drive mechanism 1 can be included in the distribution device control unit.

Figure 11:
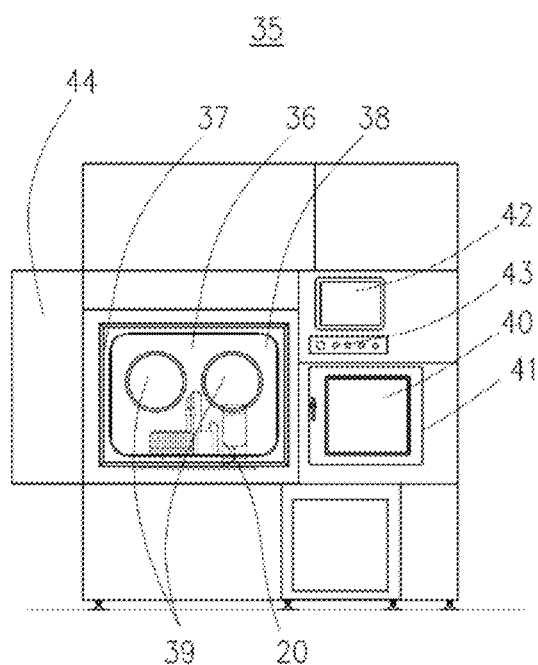
FIG. 11 is a front view illustrating an aseptic work apparatus where the distribution device according to an embodiment of the invention is disposed.
Figure 12:
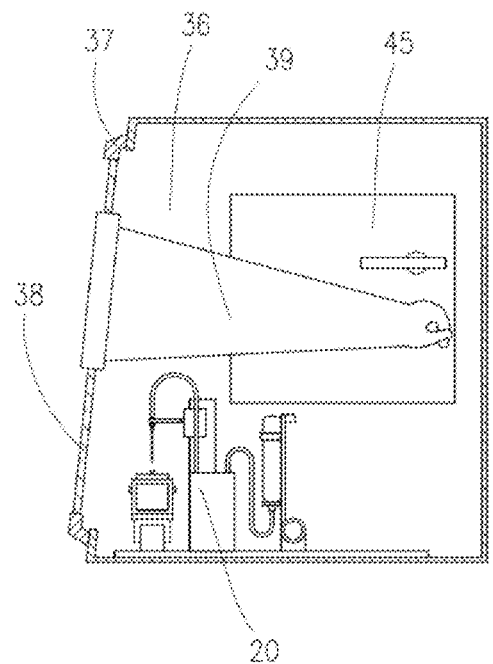
FIG. 12 is a diagram illustrating an outline of a work space provided in the aseptic work apparatus.

It should be noted that each unit constituting the distribution device 20 of the present embodiment is fixed on a base plate 34. In addition, the distribution device 20 of the present embodiment is disposed in the work space 36 of an aseptic work apparatus 35 exemplified in FIGS. 11 and 12 and capable of performing hydrogen peroxide gas sterilization. FIG. 11 is a front view exemplifying the aseptic work apparatus 35 including the distribution device 20 of the present embodiment, and FIG. 12 is a side view illustrating an outline of the internal configuration of the work space 36 of the aseptic work apparatus. The aseptic work apparatus 35 is also called an isolator. The clean work space 36 isolated from the external atmosphere is formed in the aseptic work apparatus 35. In addition, an aseptic storage apparatus 44 is coupled next to the aseptic work apparatus 35 and the communication passage between the storage of the aseptic storage apparatus 44 and the work space 36 is partitioned by a door 45 (FIG. 12). The work space 36 is maintained at a predetermined cleanliness by the clean air being circulated that has flowed in through the high efficiency particulate air (HEPA) filter (not illustrated) disposed in the upper and lower portions of the aseptic work apparatus 35.

A front door 37 capable of airtightly closing the work space 36 is attached to the front side of the work space 36, and the distribution device 20 of the present embodiment is installed in the work space 36 by the front door 37 being opened. The front door 37 is provided with a window 38 molded of transparent glass or resin such that a worker can observe the inside of the work space 36. In addition, circular openings are formed at predetermined positions of the window 38 and gloves 39 are airtightly fixed to the openings. By putting on the gloves 39 on both arms, a worker in the external environment can perform predetermined treatment on the article carried into the work space 36 while visually observing the inside of the work space 36 from the window 38. In addition, a sterilization device (not illustrated) that supplies a sterilization gas such as hydrogen peroxide vapor is connected to the aseptic work apparatus 35 of the present embodiment. The work space 36 and the distribution device 20 disposed in the work space 36 are sterilized by the work space 36 being filled with the sterilization gas supplied from the sterilization device. It should be noted that the control unit that controls the operation of the distribution device 20 of the present embodiment, the power supply unit that supplies electric power to the distribution device 20, and the control unit that controls the operation of each unit are disposed in a space in the aseptic work apparatus 35 isolated from the work space 36 in order not to be affected by the sterilization gas with which the work space 36 is filled.

In addition, the aseptic work apparatus 35 is provided with a pass box 40 adjacent to the work space 36. The pass box 40 is a box-shaped device with a sterilization function for article exchange between the work space 36 and the external environment. A sample such as a medium and an instrument having a relatively small volume and required for work in the work space 36 are brought into the work space 36 via the pass box 40. The pass box 40 includes a sterilization means for sterilizing an article brought into the internal space of the pass box 40 with ultraviolet rays or a sterilization gas, a door 41 partitioning the external environment and the internal space of the pass box 40 from each other, and a door (not illustrated) partitioning the internal space of the pass box 40 and the work space 36 from each other.

In carrying an article into the work space 36, a worker carries the article into the internal space of the pass box by opening the door 41 disposed in the front of the aseptic work apparatus 35 and then closes the door 41. Then, the internal space of the pass box 40 is sterilized. After this sterilization treatment is completed, the worker puts on the gloves 39, opens the door partitioning the work space 36 and the internal space of the pass box 40 from each other from the work space 36 side, carries the article into the work space 36, and then closes the door. As a result of the above procedure, the article carried into the work space 36 is sterilized, and thus the work space 36 is maintained in a clean state.

Next, the operation of the distribution device 20 of the present embodiment that is installed in the aseptic work apparatus 35 will be described. The container 19, the subdivision container 21, and the container rack 23 set in the distribution device 20 of the present embodiment are carried into the work space 36 via the pass box 40. With the gloves 39 on, a worker sets the subdivision container 21 in the container rack 23 and then fixes the container rack 23 on the rack placement platform 32 of the rack moving unit 24. Next, the worker connects the suction tube 30 to the discharge port 19a of the container 19 and then fixes the container 19 to the tray portion 28. Subsequently, a touch panel 42 or an operation panel 43 of the aseptic work apparatus 35 is operated and the automatic distribution operation of the distribution device 20 is initiated.

Upon receiving the operation initiation signal, the control unit operates the drive source 29 of the container holding unit 22 to rotate and move the tray portion 28 until the posture of the container 19 is inverted. Then, the control unit operates the motor 4 of the rack moving unit 24 to move the container rack 23 to a predetermined position. Here, the predetermined position is the point where the injection port 21a of the subdivision container 21 that is accommodated in the container rack 23 and disposed in the end portion of the container rack 23 is positioned directly below the nozzle 25 of the nozzle lifting-lowering unit 27. This position information is pre-stored in the control unit 70.

Next, the control unit operates the motor 4 of the nozzle lifting-lowering unit 27 to lower the nozzle 25 until the nozzle 25 is inserted through the injection port 21a of the subdivision container 21 positioned directly below the nozzle 25. Subsequently, the control unit operates the pump unit 26 to inject the medium (culture solution) with which the container 19 is filled into the subdivision container 21. After the medium (culture solution) is injected by a predetermined amount, the control unit stops the operation of the pump unit 26 and then moves the nozzle 25 up to a position away from the subdivision container 21. Subsequently, the control unit operates the motor 4 of the rack moving unit 24 to move the container rack 23 such that the subdivision container 21 next to the subdivision container 21 that has been filled with the medium (culture solution) is positioned directly below the nozzle 25. By the above procedure being repeated, the medium (culture solution) is sequentially and automatically injected into the subdivision containers 21 accommodated in the container rack 23.

After the medium (culture solution) distribution to the subdivision container 21 is completed, the worker opens the door 45, carries out the container rack 23 and the filling-completed subdivision container 21 to the storage of the storage apparatus 44, and carries the next container rack 23 and the next subdivision container 21 into the distribution device 20 from the pass box 40. In addition, if necessary, the inside of the work space 36 and the distribution device 20 are sterilized with a sterilization gas.

Figure 13:
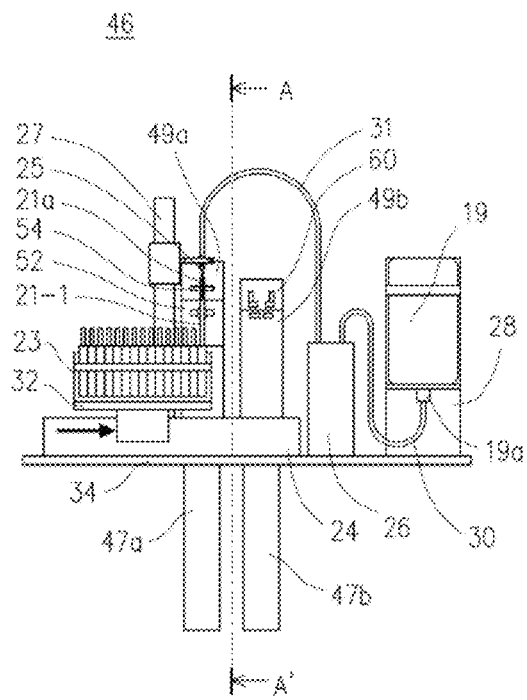
FIG. 13 is a front view illustrating an example of a state of use of a distribution sealing device according to an embodiment of the invention.
Figure 14:
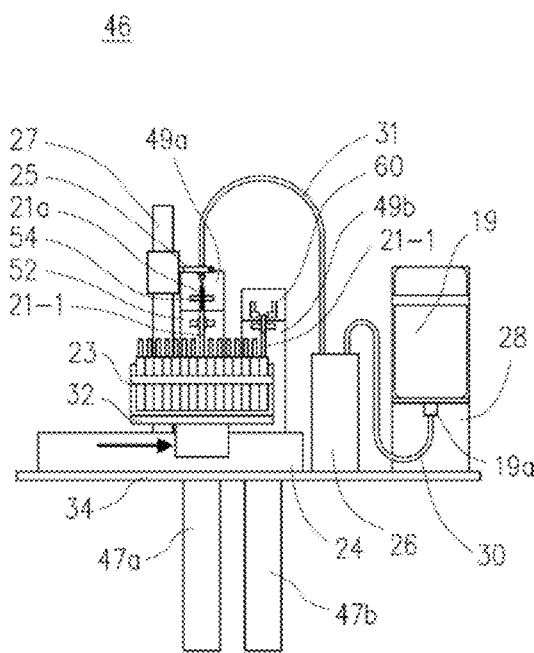
FIG. 14 is a front view illustrating another state of use of the distribution sealing device according to an embodiment of the invention.
Figure 15:
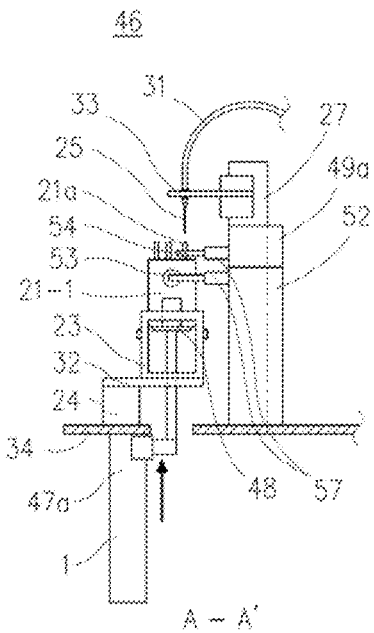
FIG. 15 is a side view illustrating a part of the distribution sealing device according to an embodiment of the invention.

Next, a distribution sealing device 46 according to another embodiment of the invention will be described. FIGS. 13 and 14 are front views illustrating the distribution sealing device 46 of the present embodiment. FIG. 15 is a side view of the distribution sealing device 46 illustrating a state where the side of a first container lifting-lowering unit 47a and a first injection assistance unit 52 is viewed from the position between the first container lifting-lowering unit 47a and a second container lifting-lowering unit 47b and the position between a first injection port holding unit 49a and a second injection port holding unit 49b in FIG. 13. The distribution sealing device 46 of the present embodiment includes the injection port holding units 49a and 49b for holding the injection port 21a of the flexible subdivision container 21 and reliably supplying a medium and a welding unit 60 for thermally welding and sealing the injection port 21a of the subdivision container 21 in addition to the distribution device 20 according to the first embodiment of the invention. Further, the distribution sealing device 46 of the present embodiment includes the two container lifting-lowering units 47a and 47b that individually lift the subdivision containers 21 stored in the container rack 23. The container lifting-lowering units 47a and 47b include a container support member 48 that supports the subdivision container 21 from below and the drive mechanism 1 that moves the container support member 48 up and down in the vertical direction. The container lifting-lowering units 47a and 47b are fixed to the lower surface of the base plate 34, and the subdivision container 21 is supported from below and moved up and down via the opening portions formed in the base plate 34 and the bottom portion of the container rack 23.

The container rack 23 where the plurality of subdivision containers 21 are accommodated side by side is moved from the left to the right in the drawing by the rack moving unit 24. As a result, the medium is sequentially injected from the subdivision container 21 at the right end. Then, the injection port 21a is sealed by the welding unit 60. This will be described in order below.

After the container rack 23 reaches a predetermined position, the first container lifting-lowering unit 47a operates to move up the subdivision container 21 that is accommodated at the right end of the container rack 23 (a first subdivision container 21-1). The first subdivision container 21-1 that has been moved up to a predetermined position by the first container lifting-lowering unit 47a is held at a position where the injection port 21a is at a predetermined height by the first injection port holding unit 49a. After the injection port 21a is held by the injection port holding unit 49, the nozzle lifting-lowering unit 27 operates, the nozzle 25 is inserted into the injection port 21a, and the medium is supplied into the first subdivision container 21-1. After the medium supply is completed, the nozzle 25 is taken out of the injection port 21a and the holding of the injection port 21a by the injection port holding unit 49 is released. Subsequently, the first subdivision container 21-1 is returned to the container rack 23 by the container lifting-lowering unit 47a being lowered.

Next, the rack moving unit 24 moves the container rack 23 to the right in the drawing until the next subdivision container 21 is positioned directly below the nozzle 25. Then, each unit sequentially performs the medium supply operation described above. In this manner, the medium is sequentially supplied to the subdivision containers 21 accommodated in the container rack 23. Then, the first subdivision container 21-1 moves to directly above the second container lifting-lowering unit 47b, the first subdivision container 21-1 is lifted to a predetermined position by the second container lifting-lowering unit 47b, and the sealing operation of the injection port 21a is initiated (see FIGS. 14 and 15). The first subdivision container 21-1 that has been moved up to the predetermined position by the second container lifting-lowering unit 47b is held by the second injection port holding unit 49b such that the injection port 21a is positioned at a predetermined position. With the injection port 21a held by the injection port holding unit 49, the injection port 21a is pressed, welded, and sealed by a heating member 66 included in the welding unit 60.

Figure 16A:
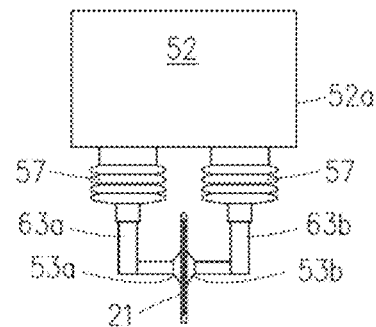
FIGS. 16A and 16B are diagrams illustrating the operation of an injection assistance unit included in the distribution sealing device.
Figure 16B:
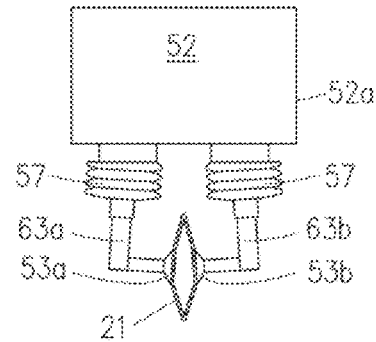

In addition, when the medium is injected from the nozzle 25, the mutually facing container wall surfaces of the subdivision container 21 are suctioned, held, and separated away from each other by the injection assistance unit 52 provided on the lower side of the first injection port holding unit 49a. FIGS. 16A and 16B are diagrams illustrating the operation of the injection assistance unit 52. All the subdivision containers 21 are manufactured by mutually facing resinous sheets being pasted together, and a large injection pressure is required to supply the medium thereinto. Accordingly, a space is formed in the subdivision container 21 and the medium is injected with ease by the injection assistance unit 52 separating the side surfaces of the container away from each other. Two suction cups 53a and 53b are provided, so as to face each other, at the parts of the injection assistance unit 52 that abut against the side surfaces of the subdivision container 21. The suction cups 53a and 53b are fixed to the tip portions of a pair of shafts 63a and 63b, respectively. The drive source provided in the injection assistance unit 52 causes the pair of shafts 63a and 63b to perform pinching operation and pinching release operation. With the subdivision container 21 completely moved up by the first container lifting-lowering unit 47a, the injection assistance unit 52 pinches the side surfaces of the subdivision container 21 from both the left and right sides. See FIG. 16A. Next, the injection assistance unit 52 adsorbs and holds both side surfaces of the subdivision container 21 with the suction cups 53a and 53b by means of the vacuum pressure from a vacuum source (not illustrated), the opening-closing mechanism provided in the injection assistance unit 52 separates both wall surfaces of the subdivision container 21 from close contact, and a space is created in the subdivision container 21. See FIG. 16B. Bellows members 57 that airtightly close the internal space of a main body casing 52a are disposed between the casing 52a of the injection assistance unit 52 and the shafts 63a and 63b. The above configuration prevents sterilization gas intrusion into the casing 52a.

Figure 17A:
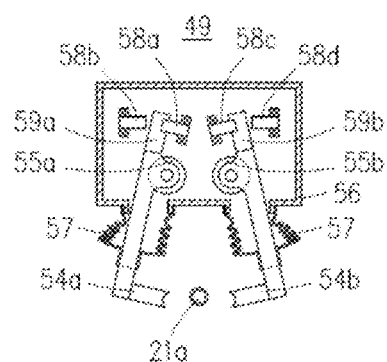
FIGS. 17A and 17B are sectional views illustrating the configuration and operation of an injection port holding unit included in the distribution sealing device.
Figure 17B:
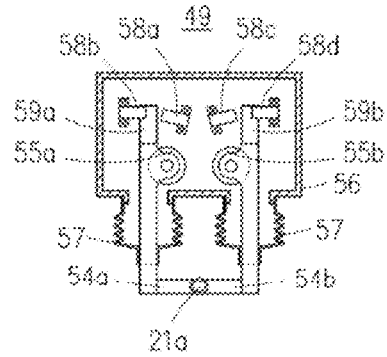

Next, the first and second injection port holding units 49a and 49b (hereinafter, simply referred to as "injection port holding unit 49" unless otherwise required) will be described. FIGS. 17A and 17B are sectional view illustrating the configuration and operation of the injection port holding unit 49. The injection port holding unit 49 is provided with a pair of bilaterally symmetrical injection port holding members 54a and 54b. The injection port 21a is held and released by the injection port holding members 54a and 54b being opened and closed. The holding unit 49 of the present embodiment includes known stepping motors 55a and 55b as drive sources opening and closing the injection port holding members 54a and 54b, respectively. The stepping motors 55a and 55b are disposed in a casing 56 included in the injection port holding unit 49. In addition, the bellows members 57 that airtightly close the internal space of the casing 56 is disposed between the injection port holding members 54a and 54b and the casing 56, respectively. The casing 56 itself is also airtightly formed, and the above configuration is capable of preventing sterilization gas intrusion into the casing 56. In addition, transmitted light sensors 58a to 58d are disposed in the casing 56 and the control unit of the welding unit 60 is capable of recognizing whether the injection port holding members 54a and 54b are open or closed by sensor dogs 59a and 59b, which are respectively disposed in the base end portions of the injection port holding members 54a and 54b, shielding the optical axes of the transmitted light sensors 58a to 58d by opening-closing operation. It should be noted that a drive mechanism similar to the mechanism described above is provided for the suction cups 53a and 53b of the injection assistance unit 52 to move to the open and closed positions.

Figure 18A:
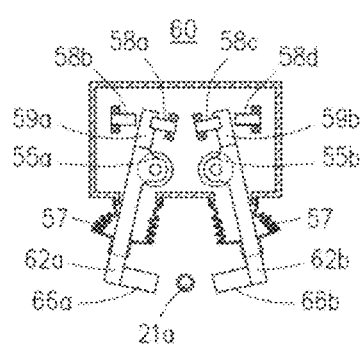
FIGS. 18A and 18B are sectional views illustrating the configuration and operation of a welding unit included in the distribution sealing device.
Figure 18B:
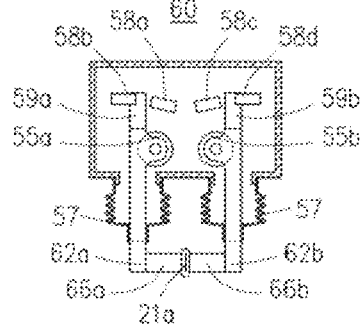

Next, the welding unit 60 will be described. FIGS. 18A and 18B are sectional views illustrating the configuration and operation of the welding unit 60. The welding unit 60 of the present embodiment is a device that seals the inside of the subdivision container 21 by thermally welding the injection port 21a of the subdivision container 21. The injection port 21a of the subdivision container 21 is formed of a thermoplastic resin such as nylon and polypropylene and can be easily sealed by heat application. In the welding unit 60 of the present embodiment, heating members 66a and 66b are fixed to the tips of a pair of shafts 62a and 62b, which move forward and backward with respect to the injection port 21a, respectively. The heating members 66a and 66b included in the welding unit 60 of the present embodiment are formed of aluminum and provided with heaters therein. As a result, the heating members 66a and 66b are heated to a temperature at which the injection port 21a can be welded. In addition, the surfaces of the heating members 66a and 66b are coated with fluororesin. As a result, the resin material of the heated injection port 21a is prevented from adhering to the heating members 66a and 66b. In addition, a drive mechanism similar to the drive mechanism included in the injection port holding unit 49 is provided for the pair of shafts 62a and 62b to move forward and backward. With the above configuration, the welding unit 60 is capable of sealing the injection port 21a by pressing the tip portion of the injection port 21a while heating the tip portion. It should be noted that the injection port 21a can be held at a predetermined position before the injection port 21a is welded and the welding can be reliably performed as a result by the injection port holding unit 49 being provided below the welding unit 60.

In addition, the second container lifting-lowering unit 47b supporting the subdivision container 21 from below is disposed below the welding unit 60 of the present embodiment and the welding unit 60 welds and seals the tip portion of the injection port 21a to the medium-injected subdivision container 21 lifted to a predetermined position by the second container lifting-lowering unit 47b. In the distribution sealing device 46 of the present embodiment, the rack 23 storing the subdivision container 21 is sequentially moved by the rack moving unit 24 as in the case of the distribution device 20 of the first embodiment. In addition, it is desirable that the separation distance between the welding unit 60 and the nozzle lifting-lowering unit 27 provided in the distribution sealing device 46 of the present embodiment is an integer multiple of the interval of the rack 23 at which the subdivision container 21 is stored. With the integer multiple of the storage interval of the subdivision container 21, the welding unit 60 is capable of sealing the injection port 21a of another, medium-injected, subdivision container 21 while the medium is injected into the subdivision container 21 stored in the rack 23 at a predetermined position.

It should be noted that devices using the drive mechanism 1 of the invention are not limited to the above-described distribution device 20 and distribution sealing device 46. For example, the drive mechanism 1 is suitable for a device that is provided with a linear motion mechanism moving an object in a linear direction and requires corrosive gas-based sterilization treatment, examples of which include a dispensing device performing cell seeding or reagent dispensing and a medium exchange device exchanging the medium (culture solution) of cells in the process of culture. In addition, the invention is not limited to devices directly related to cell culture and can be applied to, for example, a cultured cell handling device for microscopic observation in the process of cell culture or post-culture cell line division.

In addition, although permanent magnets are used for the moving-side magnet units Mg1 and Mg3 and the first biasing magnet unit Mg5 included in the movable blocks 2 and 16 in the embodiments of the invention, the invention is not limited thereto and an electromagnet may be provided instead of the permanent magnet. Further, although the ball nut 7 and the screw shaft 8 are provided as means for transmitting the drive force of the drive source 4 to the movable blocks 2 and 16 in the present embodiments, the invention is not limited thereto. For example, a drive transmission means such as a belt and a chain may be provided. Further, a linear motor may be provided instead of the drive source 4.

Although the drive mechanisms 1 and 15 of the invention have been described above with reference to the embodiments, the invention is not limited thereto and includes, for example, a change in design within a range that does not deviate from the gist of the invention.

The invention claimed is:

1. A drive mechanism comprising:
a movable block;
a drive unit configured for moving the movable block;
a guide mechanism configured for guiding the movable block in a predetermined direction;
a partition wall isolating the movable block, the drive unit, and the guide mechanism from an external environment;
a movable platform provided outside the partition wall and at a position facing the movable block via the partition wall so as to cover at least a part of the partition wall and be movable along the partition wall;
a first magnet coupling mechanism including magnets attracting each other and provided on first surfaces of the movable block and the movable platform, the first surfaces mutually facing each other via the partition wall; and
a second magnet coupling mechanism including magnets attracting each other and provided on second surfaces of the movable block and the movable platform, the second surfaces being orthogonal to the first surfaces and facing each other via the partition wall,
wherein
the movable platform is configured to move on a trajectory guided by the partition wall by following a movement of the movable block,
the drive mechanism further includes biasing magnet units provided with magnetic poles repelling each other in a direction of reinforcement of attractive force of the first magnet coupling mechanism and/or the second magnet coupling mechanism,
the biasing magnet units are provided on third surfaces of the movable block and the movable platform, the third surfaces being different from the first and second surfaces and facing each other via the partition wall, and
the third surfaces of the movable block and the movable platform where the biasing magnet units are disposed are disposed to be inclined at a predetermined angle with respect to the second surfaces of the movable block and the movable platform where the second magnet coupling mechanism is disposed.

2. The drive mechanism according to claim 1, wherein the magnets constituting the first magnet coupling mechanism and the second magnet coupling mechanism include permanent magnets.

3. The drive mechanism according to claim 2, wherein the magnets constituting the first magnet coupling mechanism and the second magnet coupling mechanism include an electromagnet.

4. A distribution device comprising the drive mechanism according to claim 1.

5. A dispensing device comprising the drive mechanism according to claim 1.

6. A medium exchange device comprising the drive mechanism according to claim 1.

7. A cultured cell handling device comprising the drive mechanism according to claim 1.

8. A drive mechanism, comprising:
a movable block;
a drive unit configured for moving the movable block;
a guide mechanism configured for guiding the movable block in a predetermined direction;
a partition wall isolating the movable block, the drive unit, and the guide mechanism from an external environment;
a movable platform provided outside the partition wall and at a position facing the movable block via the partition wall so as to cover at least a part of the partition wall and be movable along the partition wall;
a rolling body rollably attached to a surface of the movable platform facing the partition wall;
a first magnet coupling mechanism including magnets attracting each other and provided on first surfaces of the movable block and the movable platform, the first surfaces mutually facing each other via the partition wall; and
a second magnet coupling mechanism including magnets attracting each other and provided on second surfaces of the movable block and the movable platform, the second surfaces being orthogonal to the first surfaces and facing each other via the partition wall,
wherein
the movable platform is configured to move on a trajectory guided by the partition wall by following a movement of the movable block,
the drive mechanism further includes biasing magnet units provided with magnetic poles repelling each other in a direction of reinforcement of attractive force of the first magnet coupling mechanism and/or the second magnet coupling mechanism,
the biasing magnet units are provided on third surfaces of the movable block and the movable platform, the third surfaces being different from the first and second surfaces and facing each other via the partition wall, and the third surfaces of the movable block and the movable platform where the biasing magnet units are disposed are disposed to be inclined at a predetermined angle with respect to the second surfaces of the movable block and the movable platform where the second magnet coupling mechanism is disposed.

9. The drive mechanism according to claim 8, wherein the magnets constituting the first magnet coupling mechanism and the second magnet coupling mechanism include permanent magnets.

10. The drive mechanism according to claim 9, wherein the magnets constituting the first magnet coupling mechanism and the second magnet coupling mechanism include an electromagnet.

11. A distribution device comprising the drive mechanism according to claim 8.

12. A dispensing device comprising the drive mechanism according to claim 8.

13. A medium exchange device comprising the drive mechanism according to claim 8.

14. A cultured cell handling device comprising the drive mechanism according to claim 8.

15. A drive mechanism comprising:
a movable block;
a drive unit moving the movable block;
a guide mechanism guiding the movable block in a predetermined direction; and
a partition wall isolating the movable block, the drive unit, and the guide mechanism from an external environment, wherein
a substantially U-shaped movable platform is disposed so as to cover the partition wall at a position facing the movable block in the external environment defined by the partition wall,
a first drive magnet unit is provided on a first surface of the movable block,
a second drive magnet unit is provided on a second surface of the movable block orthogonal to the first surface,
a first biasing magnet unit is disposed on a surface of the movable block facing the surface where the second drive magnet unit is disposed,
a first driven magnet unit is disposed on a surface of the movable platform facing the first drive magnet unit,
a second driven magnet unit is disposed on a surface of the movable platform facing the second drive magnet unit,
a second biasing magnet unit is disposed on a surface of the movable platform facing the surface where the second driven magnet unit is disposed and facing the first biasing magnet unit of the movable block,
rolling bodies are rollably attached to the surfaces of the movable platform where the first and second driven magnet units are disposed,
the first drive and driven magnet units and the second drive and driven magnet units have magnetic poles different from each other,
the first biasing magnet unit and the second biasing magnet unit have the same magnetic poles, and
the movable platform moves in a plane defined by the partition wall by following the movement of the movable block.

16. The drive mechanism according to claim 15, wherein the magnets, which constitute the first drive magnet unit, the second drive magnet unit, the first biasing magnet unit, the first driven magnet unit, the second driven magnet and the second biasing magnet unit, include permanent magnets.

17. The drive mechanism according to claim 16, wherein the magnets, which constitute the first drive magnet unit, the second drive magnet unit, and the first biasing magnet unit, include an electromagnet.

18. A distribution device comprising the drive mechanism according to claim 15.

19. A dispensing device comprising the drive mechanism according to claim 15.

20. A medium exchange device comprising the drive mechanism according to claim 15.

21. A cultured cell handling device comprising the drive mechanism according to claim 15.

* * * * *